(12) United States Patent
Travkina et al.

(10) Patent No.: US 8,128,918 B2
(45) Date of Patent: *Mar. 6, 2012

(54) MASCARA COMPOSITION

(75) Inventors: Irina Travkina, River Edge, NJ (US); Andrew Christoforou, Monsey, NY (US); Lisa Lamberty, Hawthorne, NJ (US)

(73) Assignee: Avon Products, Inc., New York, NY (US)

(*) Notice: Subject to any disclaimer, the term of this patent is extended or adjusted under 35 U.S.C. 154(b) by 5 days.

This patent is subject to a terminal disclaimer.

(21) Appl. No.: 12/970,441

(22) Filed: Dec. 16, 2010

(65) Prior Publication Data

US 2011/0085998 A1    Apr. 14, 2011

Related U.S. Application Data

(63) Continuation of application No. 12/197,352, filed on Aug. 25, 2008, now abandoned.

(51) Int. Cl.
*A61Q 1/10* (2006.01)

(52) U.S. Cl. ...................... 424/70.7; 424/70.6

(58) Field of Classification Search .................. None
See application file for complete search history.

(56) References Cited

U.S. PATENT DOCUMENTS

| | | |
|---|---|---|
| 5,053,221 A | 10/1991 | Robertson et al. |
| 5,460,808 A | 10/1995 | Mausner |
| 5,599,547 A | 2/1997 | Bartholomey et al. |
| 5,874,072 A | 2/1999 | Alwattari |
| 6,042,815 A | 3/2000 | Keller et al. |
| 6,197,319 B1 | 3/2001 | Wang |
| 6,214,329 B1 | 4/2001 | Brieva et al. |
| 6,264,933 B1 | 7/2001 | Bodelin et al. |
| 6,274,131 B1 | 8/2001 | Piot et al. |
| 6,342,209 B1 | 1/2002 | Patil et al. |
| 7,431,919 B2 * | 10/2008 | Travkina et al. ............. 424/70.7 |

FOREIGN PATENT DOCUMENTS

EP    1110971 A    6/2001

OTHER PUBLICATIONS

Croda "2002 Year in Review", http://www.crodausa.com/datasheets/FeatureArchive/PCFeature2002YearInReview.htm.

* cited by examiner

*Primary Examiner* — Jyothsna Venkat
(74) *Attorney, Agent, or Firm* — Joan M. McGillycuddy; Charles J. Zeller

(57) ABSTRACT

Mascara compositions containing a keratin conditioning agent, alone or in combination with an emollient/moisturizing agent, provide increased resistance of eyelash hair fibers to breaking. Low viscosity mascara composition of the invention containing low concentrations of surfactant and wax are easily removable from the eyelashes. Mascara compositions of the invention reduce eyelash damage and though having low viscosity (as compared to typical prior art compositions) surprisingly provide excellent buildup, lengthening and wear.

17 Claims, 2 Drawing Sheets

MASCARA COMPOSITION

RELATED APPLICATIONS

This application is a continuation of U.S. Ser. No. 12/197,352 filed Aug. 25, 2008, the disclosure of which is incorporated by reference.

BACKGROUND OF THE INVENTION

Eye make-up/mascara cosmetic products are well known in the art. With presently marketed mascaras, thickening and lengthening of the eyelashes is typically achieved by incorporating in such products a high level of waxes and film formers. This generally leads to difficulty in washing the mascara off the eyelashes, which in turn causes damage to the eyelashes. Attempts to solve the problem by use of thin moisturizing mascaras have been unsuccessful as such products usually are not thickening or lengthening in effect. Moreover, they do not wear well and smudge and smear easily.

SUMMARY OF THE INVENTION

To remedy the deficiencies of prior art compositions, the present inventors have developed a composition that thickens and/or lengthens keratin fibers, such as eyelashes, yet is readily removable therefrom by washing. The composition of the present invention is particularly suited for application to the eyelashes. When employed for such purposes, the composition of the invention is preferably in the form of a mascara. Because the composition of the invention contains a low level of emulsifier/surfactant and of wax, damage to the eyelashes upon removal of the composition therefrom is greatly reduced. Consequently, the composition of the present invention is gentle to eyelashes.

DETAILED DESCRIPTION

Figure 1:
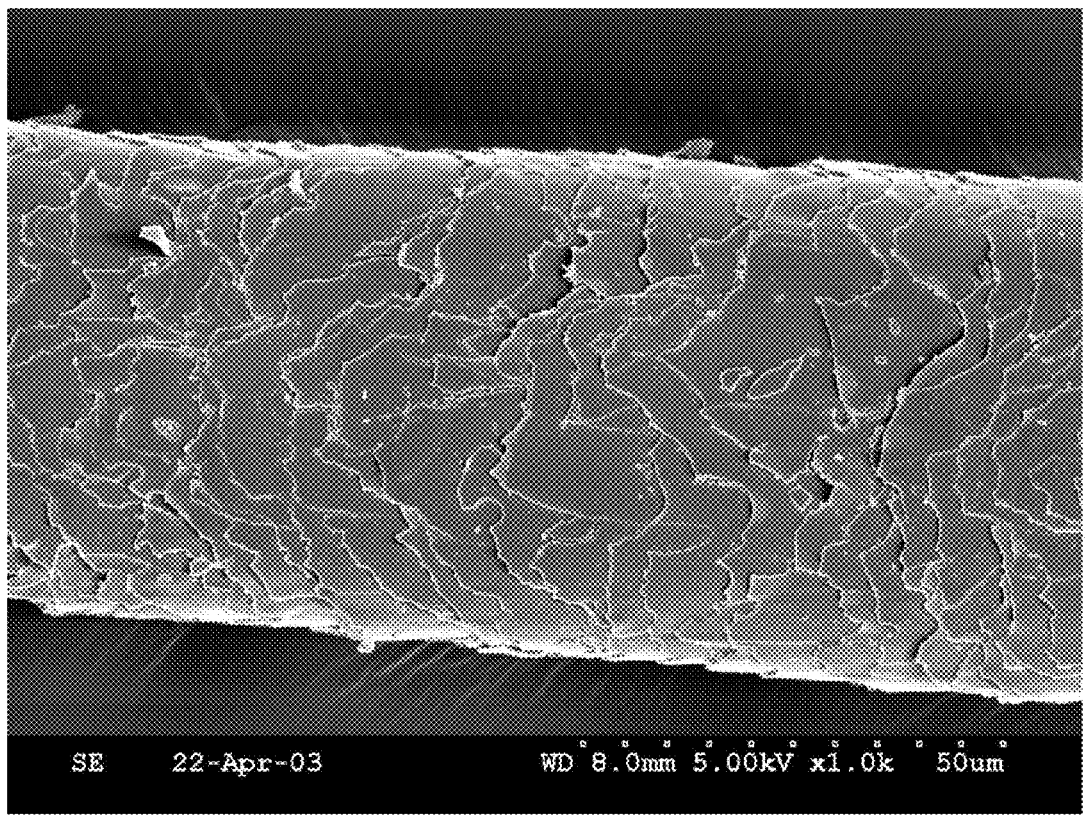
FIG. 1 is a photomicrograph of washed eyelash hair fibers before treatment with a composition of the invention.

The composition of the present invention is preferably an emulsion (also referred to herein as "mascara base"), more particularly, an oil-in-water emulsion. Most desirably, the composition of the invention is an oil-in-water emulsion based eyelash makeup.

The emulsion serves as a cosmetically acceptable vehicle for at least one cosmetically acceptable wax that is dispersed therein. Cosmetically acceptable waxes than can be employed include paraffin wax, silicon wax, microcrystalline, ozokerite, polyethylene, candelilla, carnauba, beeswax, Japan wax.

It should be noted that, unless indicated to the contrary, as used herein, percent (%) is % by weight, based on the total weight of the composition.

The amount of wax present in the composition of the invention is about 10% to about 20%, preferably about 12% to about 18%, more preferably, about 16% to about 17%, and most preferably, about 16.5%.

Preferably, a mixture of waxes is employed, at least one wax being a soft wax having a melting/softening point less than about 60° F. to about 65° F.

Suitable soft waxes have a melting point range of about 35° F. to about 65° F. They include, for example: lanolin wax, jojoba wax, jasmin wax, orange wax, olive wax and mixtures thereof.

The composition of the present invention contains from about 1% to about 10%, preferably about 1% to about 6%, more preferably, about 1% to about 3%, and most preferably, about 1.65% soft wax.

The composition of the present invention also contains from about 1% to about 10%, preferably about 2% to about 8%, more preferably about 2% to about 6% and most preferably about 3% of shellac wax (melting point of about 78° F. to about 84° F.).

As previously noted, the emulsion based vehicle of the present invention has dispersed therein at least one soft wax, preferably at least two waxes at least one of which is a soft wax.

Preferably, the composition contains about 10% to about 20% wax, of which at least one is a soft wax (melting point less than about 65° F.) and another is a wax-like material that is a natural or synthetic resin or resin derivative, such as rosinate esters, hydrogenated rosinate esters, polyamide resins, rubber, latex and shellac wax. Shellac wax is most preferred. The wax-like material is present in an amount of about 1% to about 10%.

In addition to the soft wax component(s), of the composition of the invention, one or more additional waxes can be added, for example, shellac wax (melting point of about 78° F. to about 84° F.); beeswax (melting point of about 62° F. to about 65° F.); carnauba wax (melting point of about 81° F. to about 86° F.); paraffin wax (melting point of about 69° F. to about 74° F.); and mixtures thereof.

As noted previously, the composition of the present invention is an emulsion, more particularly an oil-in-water emulsion, comprised of a water phase, in an amount of about 50% to about 75%, preferably about 55% to about 73%, more preferably, about 60% to about 70%, most preferably, about 68%, and an oil phase, in an amount of about 25% to about 50%, preferably about 25% to about 40%, more preferably, about 28% to about 32%, and most preferably, about 30%.

Generally, the amount of water present in the composition of the invention is at least about 50%, preferably, about 50% to about 60%, more preferably, about 52% to about 56%, and most preferably, about 55%.

The oil-in-water emulsion based composition of the invention is comprised of a discontinuous oil phase and a continuous water phase. An emulsifying agent is necessary to produce the emulsion.

Consequently, the composition contains at least one primary emulsifier. Preferably, the primary emulsifier is a cosmetically acceptable nonionic, anionic or amphoteric surfactant. Such materials are well known in the art. Preferably, the primary emulsifier is a salt of a fatty acid (viz a soap). More preferably, the primary emulsifier is selected from the group consisting of triethanolamine oleate, triethanolamine palmitate, triethanolamine stearate and mixtures thereof.

It should be noted that as used herein and in the claims which follow, emulsifier and surfactant are synonymous.

The primary emulsifier can be employed as such or it can be produced in situ. Triethanolamine stearate is the preferred primary emulsifier. It is employed as such or produced in situ by the reaction of triethanolamine and stearic acid.

The primary emulsifier is generally employed in an amount of less than 5%, preferably, less than 4%, more preferably, less than 3%, and most preferably, less than 2.5%.

In addition to the primary emulsifier, the composition of the present invention optionally contains at least one secondary emulsifier selected from the group consisting of glyceryl stearate, glyceryl oleate, sorbitan stearate, sorbitan laurate, sorbitan olivate, and mixtures thereof.

Generally, when present, the secondary emulsifier; or mixtures of secondary emulsifiers, is employed in an amount of about 0.5% to about 3.0%.

115 The total concentration of primary emulsifier and, when present, secondary emulsifier, is low, as compared to prior art oil-in-water emulsion based mascara compositions. The low concentration of emulsifier accounts, in part, for the mascara composition of the present invention's gentleness to eyelashes.

Prior art mascara compositions employ emulsifier/surfactant concentrations over 3%. Typically, prior art compositions contain about 5% emulsifier/surfactant. Preferred compositions of the present invention contain a low level of emulsifier/surfactant. In this regard, a low level means the composition contains 3% or less emulsifier/surfactant. More preferred compositions of the invention contain a very low level of emulsifier/surfactant. In this regard, a very low level means that the compositions contains less than 3% emulsifier/surfactant, and more preferably, about 2.5%.

Prior art mascara compositions can contain about 30% wax. Typically, they contain about 23% to about 25% wax. In contradistinction thereto, the composition of the present invention contains about 10% to about 20% wax, preferably about 16% to about 17% wax.

The lower wax content of the composition of the present invention coupled with its lower emulsifier/surfactant content makes it easy to remove the mascara composition from the eyelashes. Damage to the eyelashes is thereby greatly reduced. Thus, the composition of the present invention is gentle to eyelashes.

The composition of the present invention optionally contains one or more emollient/moisturizing oils. This constitutes a major departure from the conventional wisdom of the prior art. Prior to the present invention, inclusion of one of more oils in a mascara composition was considered undesirable as being promotive of smudging.

Emollient/moisturizing oils that can be incorporated in the composition of the invention include: jojoba oil, lanolin oil, coconut oil, palm kernel glycerides, grape seed oil, evening primrose oil, sesame oil, castor oil,meadowfoam seed oil, emu oil, dimethicone copolyol meadowfoamate, wheat germ oil, macadamia nut oil, avocado oil, and mixtures thereof.

Castor oil, emu oil, jojoba oil, wheat flour lipids, dimethicone copolyol meadowfoamate, wheat germ oil, macadamia nut oil and avocado oil are preferred.

Dimethicone copolyol meadowfoamate, wheat flour lipids, wheat germ oil, macadamia nut oil and avocado oil are more preferred.

Dimethicone copolyol meadowfoamate, wheat germ oil, macadamia nut oil, avocado oil, and mixtures thereof are most preferred.

When present in the composition of the invention, the emollient/moisturizing oil, or mixture of emollient/moisturizing oils, is generally employed in a concentration of about 0.5% to about 5%; preferably, about 1% to about 4%; more preferably, about 2% to about 3%; and, most preferably, about 2.5%.

The composition of the present invention preferably contains one or more keratin conditioning agents. Any keratin conditioning agent known to the art as cosmetically acceptable, may be employed, for example: algae extracts (for example, BIOSTRUCTURER and BIOENERGIZER from Secma), wheat amino acids, wheat protein, hydrolyzed vegetable protein, hydrolyzed vegetable protein derivatives (for example hydrolyzed vegetable protein propylene glycol-propyl silanetriol (KERAVIS from Croda Chemicals)), keratin amino acids, serum protein, yeast extract, hydrolyzed mucopolysaccharides (for example, OLIGOQUAT M from Arch Chemicals), hydrolyzed animal protein, chitosan, phytantriol, hydrolyzed corn protein, hydrolyzed soy protein, hydrolyzed silk, silk amino acids, and mixtures thereof.

Algae extracts, hydrolyzed vegetable protein, hydrolyzed vegetable protein derivatives, wheat and silk amino acids and other sources of amino acids, and hydrolyzed mucopolysaccharides are preferred.

Algae extracts, hydrolyzed vegetable protein, hydrolyzed vegetable protein derivatives and wheat and other sources of amino acids are more preferred.

Algae (Hypnea Musciforniis and Pelvetia Canalicilata and Laminaria Digitata) extracts and hydrolyzed vegetable protein propylene glycol-propyl silanetriol are most preferred. The keratin conditioning compound, or mixture of keratin conditioning compounds, is employed in an amount effective for keratin conditioning. Generally it is employed in a concentration of about 0.5% to about 5%, preferably, about 0.5% to about 3%, more preferably, about 0.5% to about 2%, and most preferably, about 0.8% to about 1%.

The composition of the invention can include agents typically included in mascara compositions, for example, preservatives, anti-foam agents, chelating agents, anti-tack agents, fillers, colorants (e.g. pigments), vitamins (e.g. panthenol), anti-oxidants, film formers, thickeners, solvents and mixtures thereof.

Any cosmetically acceptable colorant (e.g. pigment), preservative, chelating agent, filler, anti-foam agent, anti-tack agent, vitamin, anti-oxidant, film former, thickener, solvent or mixture thereof, typically employed in mascara compositions can be used in an amount typically employed for same in prior art mascara compositions.

It should be noted that the present invention also contemplates improving conventional mascaras by adding thereto a keratin-conditioning compound and/or adding an emollient/moisturizing agent in amount(s) effective to achieve the desired improvement. The improvement can be, among others, one or more of the following: conditioning of the eyelashes, moisturizing of the eyelash fibers, increasing the resistance of eyelashes to breaking. These improvements are as compared to eyelash hair fibers that have been treated with a like composition that does not contain the keratin conditioning agent and/or emollient/moisturizing agent. When the present invention is used to improve conventional mascara compositions, the conventional mascara composition may also be referred to as the "mascara base".

The mascara composition of the present invention is thin, as compared to typical mascara compositions. Compositions in accordance with the present invention have a relatively low viscosity of from about 40,000 cps to about 150,000 cps, preferably from about 40,000 cps to about 100,000 cps, more preferably, from about 40,000 cps to about 60,000 cps, most preferably about 40,000 cps to about 55,000 cps (as measured by a Brookfield viscometer at 77° F.).

Notwithstanding its low viscosity, the composition of the present invention is moisturizing, applies smoothly and has very good adhesion to the eyelashes. More importantly, the composition of the present invention imparts to the eyelashes a beneficial thickening and/or lengthening effect. These benefits are secured with a composition that is readily washed off because of its low wax and film former content.

Typically, prior art mascara compositions having a viscosity below 150,000 cps are not believed to possess the highly favorable building and lengthening properties of the composition of the present invention.

The composition of the present invention possesses outstanding adherence to keratin fibers, such as eyelashes and hair, and continues to build and lengthen with subsequent applications.

Mascaras typically require about 14 strokes of the mascara brush for satisfactory application of one coat of mascara on the eyelashes. Surprisingly, despite the thin viscosity of the composition of the present invention, its buildup is comparable to that of typically employed mascaras having much higher viscosity.

The present inventors have surprisingly discovered that when the composition of the present invention is applied to a keratin fiber (e.g. an eyelash hair fiber), the tensile strength of the fiber is increased, as compared to a keratin fiber that is not so treated. Increasing the tensile strength, in this context, means that a keratin fiber, such as an eyelash, treated with a composition in accordance with the present invention, requires substantially more force before it will break, as compared to a like keratin fiber that has not been treated with the composition of the present invention.

Tests carried out by the present inventors have shown that eyelash hair fibers treated with a composition of the present invention require about 35% more force to break than untreated eyelash hair fibers. It is possible that the treated eyelash hair fibers surprising increased resistance to breaking is attributable to the keratin conditioning component(s) of the composition of the invention. However, the emollient/moisturizing oil component(s) of the composition, not heretofore employed in mascara compositions, may also play a role.

The following contemplated examples are offered solely for the purpose of illustrating the invention and are not intended to limit the scope of the invention in any respect.

EXAMPLES 1-3

| Components | Ex. 1 | Ex. 2 | Ex. 3 |
|---|---|---|---|
| Polyvinylpyrrolidone | 1 | 2 | 1 |
| Gum arabic | 0.1 | — | 0.3 |
| Sodium carboxymethyl cellulose | 0.5 | 0.2 | 0.2 |
| Methylparaben | 0.4 | 0.3 | 0.4 |
| Triethanolamine | 1.1 | 1.3 | 1 |
| Tetrasodium EDTA | 0.1 | — | — |
| Dimethicone copolyol meadowfoamate | 2.5 | 2 | 3 |
| Iron oxide-black | 8 | 9 | 10 |
| Pentaerythritol tetrastearate | 0.5 | — | 2 |
| Shellac wax 100% | 5 | 3 | 3 |
| Carnauba wax | 3 | 4 | 3 |
| Hydrogenated olive oil | 0.5 | — | — |
| Orange (citrus aurantium dulcis) peel wax | 0.8 | 0.5 | 0.2 |
| Olive oil | 1 | 0.7 | 0.7 |
| Beeswax | 2 | 5 | 5 |
| Paraffin wax 165 | 5 | 5 | 5 |
| Cetearyl olivate | 2.5 | — | 1.1 |
| Sorbitan olivate | 1 | — | 1.1 |
| Stearic acid | 3 | 3.5 | 3.4 |
| Propylparaben | 0.2 | 0.2 | 0.2 |
| Wheat germ oil | 0.1 | 0.5 | 0.5 |
| Macadamia nut oil | 0.1 | — | — |
| Panthenol | 0.4 | 0.3 | 0.3 |
| Benzyl alcohol | 0.8 | 0.5 | 0.5 |
| Avocado oil | 0.6 | — | — |

-continued

| Components | Ex. 1 | Ex. 2 | Ex. 3 |
|---|---|---|---|
| Nylon powder | 0.5 | — | — |
| Wheat flour lipids | 0.5 | — | — |
| Algae extract | 0.3 | 0.1 | 0.1 |
| Hydrolyzed wheat starch | 0.2 | — | — |
| Isododecane | 1.4 | 1 | 0.8 |
| Ethylene/propylene/styrene copolymer | 0.5 | 0.5 | 0.4 |
| Acrylates copolymer | 1 | — | 0.5 |
| Sodium polyaspartate | 0.2 | — | 0.1 |
| Wheat amino acid | 0.3 | 0.2 | 0.2 |
| Hydrolyzed soy protein | 0.3 | 0.1 | 0.1 |
| Soy oligosaccharides | 0.3 | — | — |
| Demineralized water | QS | QS | QS |
| TOTAL | 100% | 100% | 100% |

The following Example 4 serves to provide a general formula of representative oil-in-water emulsion based mascara compositions in accordance with the present invention. Suggested ingredients ranges are provided.

EXAMPLE 4

| | Component | Range |
|---|---|---|
| A. Water Phase | Gums/thickeners | 0.2-1% |
| | Film formers | 0.5-1% |
| | Preservative | 0.1-0.6% |
| | Chelating agent | 0.1-0.4% |
| | Antifoam agent | 0.1-0.4% |
| | Base (e.g. triethanoloamine) | 1-2.5% |
| | Pigment | 4-10% |
| | Water | qs 100% |
| B. Oil Phase | Waxes | 10-20% |
| | Orange wax | 1-10% |
| | Shellac wax | 1-10% |
| | Surfactant/emulsifiers | 2-5% |
| | Emollients (e.g. oils & esters) | 0.5-5% |
| C. Fillers | | 0.2% |
| D. Temperature Sensitive Components | Acrylates copolymer | 0.5% |
| | Hydrolyzed soy protein | 0.1-0.5% |
| | Algae extracts | 0.5% |
| | Wheat amino acids | 0.5% |
| | Soy oligosaccharides | 1% |

The compositions of Examples 1-4 are prepared in accordance with the following procedure:

(a) The water phase (e.g. gums/thickeners, film formers, preservatives, chelating agents, antifoam agents, base and pigments) is heated to a temperature of about 185° F. then the pigment is dispersed therein under agitation.

(b) The oil phase (e.g. waxes, emulsifier/surfactants, emollient oils and esters) is heated to a temperature of about 185° F.

(c) The oil and water phases are mixed and homogenized with the aid of a high shear homogenizer.

(d) The fillers are added to the resultant emulsion.

(e) When the emulsion reaches room temperature, the temperature sensitive components (e.g. acrylates copolymer, hydrolyzed soy protein, algae extracts, wheat amino acids and soy oligosaccharides) are dispersed therein.

Tests were conducted to substantiate the surprising benefits of the mascara compositions of the present invention. The tests and test results are as detailed in Examples 5 and 6 which follow.

EXAMPLE 5

Washed eyelash hair fibers were examined under an instrument and a photomicrograph was taken of the washed eyelash hair fibers before they were treated. This served as a control (see FIG. 1). One coat (14 strokes) of a mascara composition of the present invention (for example, the composition of Example 1) was applied to human eyelash fibers and allowed to remain in place for 8 hours. The mascara was then washed off with soap and water.

Figure 2:
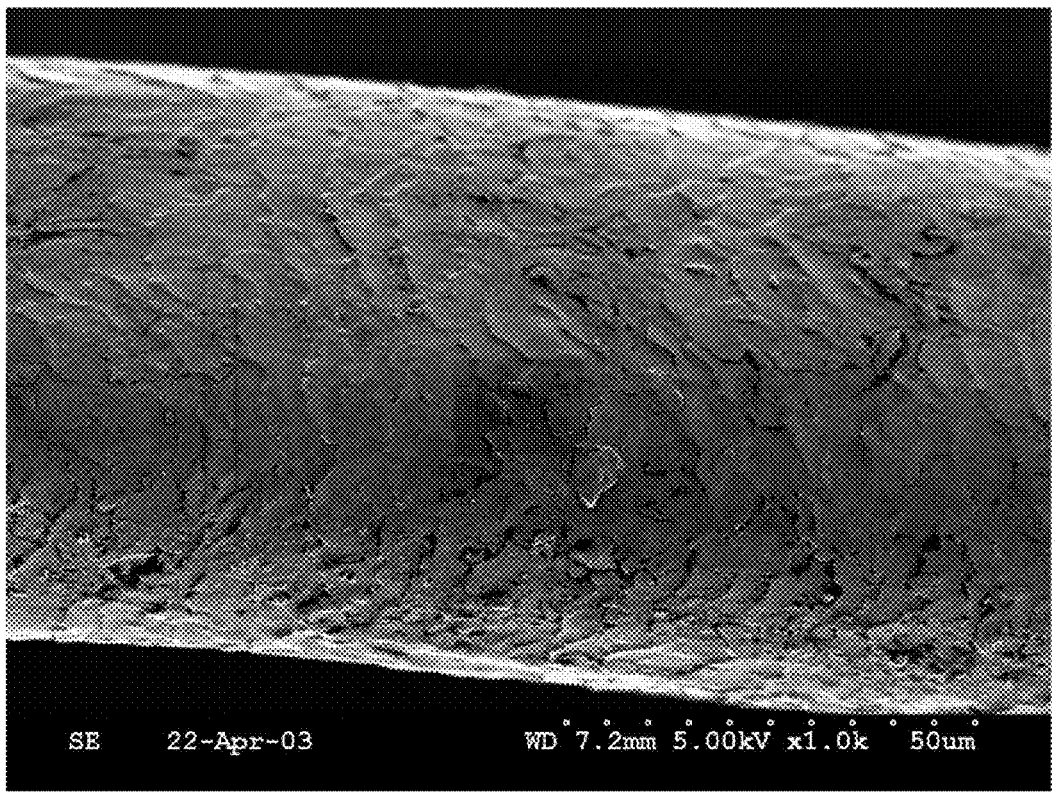
FIG. 2 is a photomicrograph of the washed eyelash hair fibers of FIG. 1, after they have been treated with a composition of the invention and the composition has been washed off.

FIG. 2 is a photomicrograph taken of the treated and washed eyelash hair fiber. A comparison of the photomicrographs of FIGS. 1 and 2 clearly shows that, as is shown in FIG. 1, prior to application of the composition of the invention and its removal, the cuticle of the hair fiber was very rough and very irregular. The cuticle can be seen to be actually lifting in a number of areas. As evidenced by FIG. 2, after the application of the composition of the present invention to the hair fiber and washing it off, the surface of the hair fiber became more even and evidenced little or no lifting.

Though not wishing to be bound by any particularly theory, it may be that the smoothing of the surface of the hair fiber is attributable to one or more of the conditioning and/or film forming components of the composition of the invention being substantive to the hair surface and remaining thereon even after washing.

EXAMPLE 6

The following study was carried out to compare the effect of a mascara composition of the present invention (containing a keratin conditioning agent and an emollient/moisturizing agent), and that of a like mascara (but not containing the keratin conditioning agent and emollient/moisturizing agent) on the flexabrasion lifetime of virgin European brown hair (ex De Meo). Virgin European hair was used as a suitable comparison fiber to eyelashes.

The Flexabrasion is a specially built piece of equipment designed to assess the fatigue lifetime of a strand of hair through bending and straightening. It is designed to mimic the interaction of hair against hair on the human head when it is being brushed. When a brush is pulled through the hair, the hair strands are entwined and move against one another causing longitudinal shear within the fiber shaft, abrasion and extension of the hair fiber, which will eventually cause longitudinal splitting and premature fracture.

Damage to the hair shaft is simulated as each strand of hair is moved backwards and forwards over a piece of drawn rough Tungsten wire. The test method enables the evaluation of the effect of actives on fatigue lifetime.

The flexabrasion allows simultaneous testing of 20 hair segments. Positioning same in a humidity-controlled cabinet, permits monitoring of the relative humidity under which the hair is being tested.

Test Procedure:

Three (3) adjacent segments of 14 mm were cut from the root end of the hair. Care was taken to avoid touching the hair segments. The first segment was cut from as close as possible to the root and was labeled either segment B or C. The next segment was cut adjacent to the first and was labeled segment A, the final segment was cut adjacent to the second and labeled C or B accordingly.

The root end of each segment was then attached to a flattened crimp using cyanoacrylate glue. When the latter had dried, the other end was glued to another flattened crimp. This gave 10 mm of hair segment between the crimps, suitable for testing. This procedure was repeated to prepare all the segments. The segments were then treated as follows:

1. The A segments were left for 17 hours at ambient relative humidity and temperature and then soaked in 2% sodium laureth sulfate (SLES) at 35° C. for 2 minutes, rinsed and allowed to dry under ambient conditions.
2. The control mascara was applied to the B segments using a fine paintbrush. The B segments were then kept at ambient relative humidity (RH) and temperature for 17 hours. They were then soaked in 2% SLES at 35° C. for 2 minutes, then rinsed and allowed to dry under ambient conditions.
3. The mascara composition in accordance with the present invention was applied to the C segments using a fine paintbrush. The C segments were then kept at ambient RH and temperature for 17 hours. They were then soaked in 2% SLES at 35° C. for 2 minutes, then rinsed and allowed to dry under ambient conditions.

The segments were then mounted onto the flexabrasion machine. One crimp was passed over the drawn tungsten wire (0.2 mm diameter) and fixed in the holder. The weight was then attached on to the other crimp and fixed in place. Each mounted sample was not initially placed under the tension of the hanging weight. The weights were balanced so that the hair segment was not under tension and allowed to equilibrate for 1 hour at 60% RH. The hair segment was then lowered into position to initiate testing.

The tests were carried out in a humidity controlled cabinet at 60% RH. The test results were analyzed statistically using the student t-test.

A percentage calculation was used to report the results in a format expressing the effect of the treatment on the segments compared to the control. The calculation is as follows:

$$\text{Percentage Difference} = ((B-A)/A) \times 100$$

Where:
A=Control segments fatigue lifetime
B=Test segments fatigue lifetime
This was calculated for each set of segments before being averaged.

This calculation gives a percentage increase or decrease.

The results clearly show statistically significant differences between the hair segments treated with mascara and the segments treated with SLES only.

|  | Control Mascara vs Untreated % Difference | Mascara Composition of the Present Invention vs Untreated % Difference |
| --- | --- | --- |
| Population | 36 | 36 |
| Mean | 24 | 28 |
| t | 1.79 | 2.34 |
| p | p < 0.01 | p < 0.05 |

Note:
This percentage difference is directly calculated against flexabrasion fatigue lifetime of the segments treated with 2% SLES only (untreated).

Both mascaras appear to provide benefits to the segments either by strengthening or by protection against the 2% SLES. The control mascara alone provided a 24% (p<0.01) improvement in flexabrasion lifetime in comparison to the untreated segments, whereas the mascara composition of the present invention gave a larger improvement of 28% (p<0.05).

Mascara Composition of

| | the Present Invention vs Control Mascara % Difference |
|---|---|
| Population | 36 |
| Mean | 35 |
| T | 2.06 |
| P | p < 1.05 |

Note:
This percentage difference is directly calculated against flexabrasion fatigue lifetime of the fibers treated by the control mascara.

A comparison of the segments treated with the mascara composition of the present invention to the control mascara (remembering that in this calculation the percentage difference is calculated against the control mascara) shows that an improvement of 35% (p<1.05) is obtained in terms of effect on flexabrasion fatigue lifetime of the hair.

The test results clearly demonstrate that the mascara composition of the present invention performed 35% (p<1.05) better in terms of improvement of flexabrasion fatigue lifetime than the comparison control mascara composition.

When comparing the effect of the two mascaras on the test hair segments to the untreated hair segments, improvements in flexabrasion fatigue lifetime of 28% (p<0.05) and 24% (p<0.01) were observed respectively, for the mascara composition of the present invention and the control mascara composition.

It should be understood that the foregoing description is only illustrative of the present invention. Various alternatives and modifications can be devised by those skilled in the art without departing from the invention. Accordingly, the present invention is intended to embrace all such alternatives, modifications and variances that fall within the scope of the appended claims.

What is claimed is:

1. A mascara composition comprising a mascara base and a keratin conditioning agent in an amount effective to improve the aesthetic appearance of a keratinous fiber to which said mascara composition is applied, wherein the mascara base is an oil-in-water emulsion comprised of a water phase in an amount of about 50 weight % to about 75 weight % and an oil phase in an amount of about 25 weight % to about 50 weight % of the total composition; and wherein the mascara base comprises:
(a) about 10 weight % to about 20 weight % of a cosmetically acceptable wax consisting essentially of a mixture of:
(i) about 1 weight % to about 10 weight % of at least one soft wax having a melting/softening point of about 35° F. to about 65° F., and
(ii) about 1 weight % to about 10 weight % of a material that is a natural or synthetic resin or resin derivative;
(b) a cosmetically acceptable emulsifier in amounts less than about 2.5 weight %; and about 0.5 weight % to about 5 weight % of at least one keratin conditioning agent selected from the group consisting of algae extracts, wheat amino acids, wheat protein, hydrolyzed vegetable protein, hydrolyzed vegetable protein derivatives, keratin amino acids, serum protein, yeast extract, hydrolyzed mucopolysaccharides, hydrolyzed animal protein, chitosan, phytantriol, hydrolyzed corn protein, hydrolyzed soy protein, hydrolyzed silk, silk amino acids, and mixtures thereof; and wherein the viscosity of said mascara composition varies from about 40,000 cps to about 150,000 cps, as measured by a Brookfield viscometer at 77° F.; wherein said composition is adapted to be gentle to eyelashes and readily washed off.

2. A method for increasing the resistance of hair fibers of eyelashes to breaking comprising treating the eyelashes with an amount of a keratin conditioning agent effective to increase the resistance of the eyelash hair fibers to breaking as compared with eyelash hair fibers untreated with the keratin conditioning agent comprising applying to the eyelashes a mascara composition comprising a mascara base and a keratin conditioning agent in an amount effective to improve the aesthetic appearance of a keratinous fiber to which said mascara composition is applied, wherein the mascara base is an oil-in-water emulsion comprised of a water phase in an amount of about 50 weight % to about 75 weight % and an oil phase in an amount of about 25 weight % to about 50 weight % of the total composition; and wherein the mascara base comprises:
(a) about 10 weight % to about 20 weight % of a cosmetically acceptable wax consisting essentially of a mixture of:
(i) about 1 weight % to about 10 weight % of at least one soft wax having a melting softening point of about 35° F. to about 65° F., and
(ii) about 1 weight % to about 10 weight % of a material that is a natural or synthetic resin or resin derivative;
(b) a cosmetically acceptable emulsifier in amounts less than about 2.5 weight %; and about 0.5 weight % to about 5 weight % of at least one keratin conditioning agent selected from the group consisting of algae extracts, Wheat amino acids, wheat protein, hydrolyzed vegetable protein, hydrolyzed vegetable protein derivatives, keratin amino acids, serum protein, yeast extract, hydrolyzed mucopolysaccharides, hydrolyzed animal protein, chitosan, phytantriol, hydrolyzed corn protein, hydrolyzed soy protein, hydrolyzed silk, silk amino acids, and mixtures thereof; and wherein the viscosity of said mascara composition varies from about 40,000 cps to about 150,000 cps, as measured by a Brookfield viscometer at 77° F., wherein said composition is adapted to be gentle to eyelashes and readily washed off 3. The mascara composition of claim 1, wherein the keratin conditioning agent is selected from the group consisting of algae extracts, hydrolyzed vegetable protein and its derivatives, wheat and silk amino acids, hydrolyzed mucopolysaccharides, and mixtures thereof 4. The mascara composition of claim 1, wherein the hydrolyzed vegetable protein derivative is hydrolyzed vegetable protein propylene glycol-propyl silanetriol.

5. The mascara composition of claim 1, wherein the keratin conditioning agent is present in an amount of about 0.5% to about 3%.

6. The mascara composition of claim 1, further comprising an emollient/moisturizing agent in an amount effective to moisturize eyelash fibers when the mascara composition is applied thereto.

7. The mascara composition of claim 6, wherein the emollient/moisturizing agent is selected from the group consisting of jojoba oil, lanolin oil, coconut oil, palm kernel glycerides, grape seed oil, evening primrose oil, sesame oil, castor oil, meadowfoam seed oil, emu oil, dimethicone copolyol meadowfoamate, wheat germ oil, macadamia nut oil, avocado oil, and mixtures thereof.

8. The mascara composition of claim 6, wherein the emollient/moisturizing agent is selected from the group consisting of castor oil, emu oil, jojoba oil, wheat flour lipids, dimethicone copolyol meadowfoamate, wheat germ oil, macadamia nut oil, avocado oil, and mixtures thereof.

9. The mascara composition of claim 6, wherein the emollient/moisturizing agent is selected from the group consisting of dimethicone copolyol meadowfoamate, wheat flour lipids, wheat germ oil, macadamia nut oil, avocado oil, and mixtures thereof.

10. The mascara composition of claim 6, wherein the emollient/moistuizing agent is selected from the group consisting of dimethicone copolyol meadowfoamate, wheat germ oil, macadamia nut oil, avocado oil, and mixtures thereof.

11. The mascara composition claim 6, wherein the emollient/moisturizing agent is present in an amount of about 0.5% to about 5%.

12. The mascara composition of claim 6, wherein the emollient/moisturizing agent is present in an amount of about 2.5%.

13. The mascara composition of claim 6, wherein the keratin conditioning agent is present in an amount of about 0.5% to about 5%; and the emollient/moisturizing agent is present in an amount of about 0.5% to about 5%.

14. The mascara composition of claim 1, wherein the mascara composition has a viscosity of from about 40,000 cps to about 100,000 cps, as measured by a Brookfield viscometer at 77° F.

15. The mascara composition, of claim 1, wherein the mascara base contains about 16% to about 17% cosmetically acceptable wax, based upon the total weight of the mascara composition.

16. The mascara composition of claim 1, wherein the keratin conditioning agent is present in an amount effective to condition the eyelashes when the mascara composition is applied thereto.

17. The mascara composition of claim 1, wherein the keratin conditioning agent is present in an amount effective to increase the resistance of eyelash hair fibers to breaking, as compared to eyelash hair fibers that have been treated with a mascara composition that does not contain the keratin conditioning agent.

* * * * *